US012797424B2

(12) United States Patent
Katsuda et al.

(10) Patent No.: US 12,797,424 B2
(45) Date of Patent: Nov. 17, 2026

(54) METHOD FOR TREATING GLAUCOMA AND METHOD FOR LOWERING INTRAOCULAR PRESSURE

(71) Applicant: PLUM Co., Ltd., Aichi (JP)

(72) Inventors: Itsuro Katsuda, Aichi (JP); Kazuharu Suzuki, Aichi (JP); Akio Inoue, Aichi (JP); Tsuguyo Yamazaki, Aichi (JP); Yu Inoue, Aichi (JP); Fumiya Mizutani, Aichi (JP); Motoko Mizutani, Aichi (JP)

(73) Assignee: PLUM CO., LTD., Aichi (JP)

( * ) Notice: Subject to any disclaimer, the term of this patent is extended or adjusted under 35 U.S.C. 154(b) by 486 days.

(21) Appl. No.: 18/513,955

(22) Filed: Nov. 20, 2023

(65) Prior Publication Data

US 2025/0161388 A1 May 22, 2025

(51) Int. Cl.

*A61K 36/19* (2006.01)
*A61K 9/00* (2006.01)
*A61P 27/06* (2006.01)

(52) U.S. Cl.

CPC .............. *A61K 36/19* (2013.01); *A61P 27/06* (2018.01); *A61K 9/0053* (2013.01)

(58) Field of Classification Search

None

See application file for complete search history.

(56) References Cited

U.S. PATENT DOCUMENTS

| | | | |
|---|---|---|---|
| 8,258,131 | B2 | 9/2012 | Takahashi et al. |
| 9,364,438 | B2 | 6/2016 | Murata et al. |
| 10,231,929 | B2 | 3/2019 | Nomura et al. |

FOREIGN PATENT DOCUMENTS

| | | | | |
|---|---|---|---|---|
| CN | 102058502 | A | | 5/2011 |
| EP | 1 621 199 | B8 | | 11/2010 |
| JP | 10-29927 | A | | 2/1998 |
| JP | 2000-143437 | A | | 5/2000 |
| JP | 2010-13400 | A | | 1/2010 |
| JP | 5357027 | B2 | | 12/2013 |
| JP | 5765687 | B2 | | 8/2015 |
| JP | 6225113 | | | 11/2017 |
| JP | 6245786 | B2 | | 12/2017 |
| JP | 2019-81741 | A | | 5/2019 |
| JP | 6537147 | B2 | | 7/2019 |
| JP | 2020-121959 | A | | 8/2020 |
| JP | 2022-176422 | | * | 11/2022 |
| WO | 2004/091630 | A1 | | 10/2004 |

OTHER PUBLICATIONS

Limsong et al., "Inhibitory effect of some herbal extracts on adherence of Streptococcus mutans", Journal of Ethnopharmacology 92, 2004, pp. 281-289.

* cited by examiner

*Primary Examiner* — Michael V Meller

(74) *Attorney, Agent, or Firm* — Greenblum & Bernstein, P.L.C.

(57) ABSTRACT

A method for treating glaucoma and a method for lowering intraocular pressure of the invention are excellent methods because the safety is high, ingestion can be carried out on a daily basis, and the methods only involves administering green chiretta.

4 Claims, No Drawings

METHOD FOR TREATING GLAUCOMA AND METHOD FOR LOWERING INTRAOCULAR PRESSURE

BACKGROUND OF THE INVENTION

1. Field of the Invention

The present invention relates to a method for treating glaucoma and a method for lowering intraocular pressure.

2. Description of Related Art

Glaucoma usually refers to a condition where the pressure in the eyeball (intraocular pressure) is abnormally increased, and is caused by various factors, and is also triggered by overwork, lack of sleep, or the like. Glaucoma leads to blurred vision, seeing rainbow halos (seeing rainbow-like rings around lights), eye pain and a headache, and in severe cases, blindness. This name comes from the fact that the color of the pupil that has lost vision appears green. Glaucoma is also called “Aosokohi (green shadow in the bottom)”.

Glaucoma includes not only high-tension glaucoma, in which the intraocular pressure is 21 to 22 mmHg or higher, but also normal-tension glaucoma, which causes visual field defects even when the intraocular pressure is within the normal range of 10 mmHg to 20/21 mmHg. Glaucoma includes not only open-angle glaucoma including high-tension glaucoma and normal-tension glaucoma, but also angle-closure glaucoma, and further includes secondary glaucoma and congenital glaucoma in addition to primary glaucoma including open-angle glaucoma and angle-closure glaucoma.

The open-angle glaucoma including high-tension glaucoma and normal-tension glaucoma is mostly chronic glaucoma, and visual field defects progress slowly. The angle-closure glaucoma is acute glaucoma, in which the drainage angle serving as the outlet for the aqueous humor inside the cornea is closed, causing a sudden rise in intraocular pressure, and if treatment is delayed, blindness may result, therefore urgent treatment is required.

The secondary glaucoma is glaucoma caused by increased intraocular pressure due to trauma, a corneal disease, retinal detachment, a brain disease, diabetes, uveitis, eye inflammation, or an eye disease, and increased intraocular pressure due to a drug such as a steroid hormone preparation.

The congenital glaucoma includes early-onset developmental glaucoma that occurs before one year of age, late-onset developmental glaucoma that occurs in the teens and twenties, and other conditions such as aniridia, Sturge-Weber syndrome, and Peters anomaly. The symptoms are excessive tear production, twitching of an eyelid, an enlarged eye, a white cloudy eye, or abnormally disliking light or the like.

The abnormal intraocular pressure is defined as 21 to 22 mmHg or higher, which is an indicator for diagnosis. However, there are individual differences, and some people have no abnormality in their visual field even when the intraocular pressure is 21 to 22 mmHg or higher, while others have an abnormality in their visual field even when the intraocular pressure is 21 to 22 mmHg or lower. Thus there are large individual differences, and it is difficult to make a general statement.

CITATION LIST

Patent Literature

PTL 1: JP2020-121959A
PTL 2: JP2019-081741A
PTL 3: JPH10-029927A
PTL 4: JP2010-013400A
PTL 5: CP102058502A
PTL 6: JP2000-143437A
PTL 7: JP6245786B
PTL 8: JP6225113B
PTL 9: JP6537147B
PTL 10: JP5765687B
PTL 11: WO2004/091630
PTL 12: JP5357027B

Non Patent Literature

NPL 1: Journal of Ethnopharmacology, 2004, vol. 92, pp. 281-289

SUMMARY OF THE INVENTION

The invention has been made to solve the above-mentioned problems, and an object of the invention is to provide a method for treating glaucoma and a method for lowering intraocular pressure as described above. The “treatment” as used herein includes improving a glaucomatous disease, treating and improving glaucoma, stopping the progression of glaucoma, and delaying the progression of glaucoma in addition to curing a glaucoma lesion. Furthermore, the phrase “lowering intraocular pressure” as used herein refers to decreasing intraocular pressure, preferably decreasing intraocular pressure that is higher than a normal value to a normal value, or lowering intraocular pressure within a normal value range even if it is within the normal value range.

As a result of intensive studies to solve the problems, the present inventors found that green chiretta has excellent effects of treating glaucoma and lowering intraocular pressure, and thus completed the invention.

That is, the invention is directed to a method for treating glaucoma including administering green chiretta to a mammal.

In addition, the invention is directed to a method for lowering intraocular pressure including administering green chiretta to a mammal.

Green chiretta, which is used in the method for treating glaucoma and the method for lowering intraocular pressure of the invention, has been used as an herb or an herbal medicine for maintaining health for many years, and is highly safe. It is possible to obtain an excellent therapeutic effect on glaucoma and an excellent effect of lowering intraocular pressure by ingesting green chiretta.

DESCRIPTION OF EMBODIMENTS

First, the method for treating glaucoma of the invention will be described.

The method for treating glaucoma of the invention includes administering green chiretta to a mammal.

Green chiretta (scientific name: *Andrographis paniculata*) is a plant of the genus *Andrographis* in the family Acanthaceae, and is an annual plant with a height of 0.5 to 1 m with branches and leaves growing abundantly in Southeast Asian countries such as India, Pakistan, Sri Lanka, and Indonesia. Green chiretta contains a diterpene lactone compound such as andrographolide. There are no particular restrictions on a part of green chiretta used in the invention, and leaves, stems, roots, flowers, seeds, fruits, a whole plant, or the like can be used. Among these parts, it is preferred to use leaves because leaves contain 2 mass % or more of andrographolide (diterpene lactone). As the green chiretta, which is the active ingredient of the invention, a plant body as it is, juice obtained by squeezing a plant body, a dried product obtained by drying a plant body, a ground material of the dried product, an extract extracted therefrom, and the like are included, but a material obtained by grinding green chiretta is preferred from the viewpoint of the therapeutic effect on glaucoma, or the like.

The method of grinding green chiretta is not particularly limited, and examples thereof include a method in which green chiretta is dried, cut to an appropriate size, sterilized, and then ground with a grinder such as a hammer mill, a mill, a mortar, or a stone mill. The size of green chiretta after grinding is not particularly limited, but is, for example, about 1 mm to 1 μm, and preferably about 1 mm to 10 μm.

The method of extracting green chiretta with a solvent is not particularly limited, and for example, green chiretta may be immersed in water, an alcohol, a liquid oil, or the like, and extracted as appropriate at normal temperature or the like.

The form of green chiretta used in the method for treating glaucoma of the invention is not particularly limited, and green chiretta can be formed into a pharmaceutical preparation, a quasi-drug, a food or drink, a supplement, or the like for humans. As for a pharmaceutical preparation or a quasi-drug, green chiretta can be formulated as it is, or by being combined with a pharmaceutically acceptable carrier as needed. Further, if necessary, a conventional additive can also be added as appropriate. The dosage form is not particularly limited, but is preferably a dosage form that can be ingested orally because the effect can be exhibited through the mouth, and examples thereof include a capsule, a liquid, a powder, a granule, and a tablet. These can be produced according to a conventional method.

When green chiretta is formed into a food or drink, a food or drink can be prepared according to a conventional method using green chiretta as it is or by blending a known food additive or a food material as needed. The mode is not particularly limited, and examples thereof include foods such as bread, cookies, cakes, and noodles, confectionery such as gum, candies, and Japanese sweets, meat foods such as ham and sausages, fish foods such as chikuwa fish cake and kamaboko fish cake, seafood foods, seasonings such as dressings, soy sauce, jam, and furikake condiment, beverages such as tea, juices, soft drinks, and alcohols, and in addition thereto, functional foods, foods for specified health uses, and foods with functional claims formed into a form similar to that of the above-mentioned pharmaceutical preparation or the like (a capsule, a liquid, a powder, a granule, or a tablet).

Glaucoma can be treated by administering green chiretta described above to a mammal. Here, glaucoma includes not only open-angle glaucoma including high-tension glaucoma and normal-tension glaucoma, but also angle-closure glaucoma, and further includes secondary glaucoma and congenital glaucoma in addition to primary glaucoma including open-angle glaucoma and angle-closure glaucoma. Glaucoma that can be treated by the invention is preferably open-angle glaucoma, more preferably high-tension glaucoma or normal-tension glaucoma.

Examples of the mammal include humans, dogs, cats, guinea pigs, and rabbits, and humans are preferred.

By administering green chiretta, it is possible to observe reduction or disappearance of visual field defects (visual field defects disappear) due to glaucoma as compared to before administration. The method of administering green chiretta in the method for treating glaucoma of the invention is not particularly limited, but oral administration is preferred because the effect can be exhibited through the mouth.

In the method for treating glaucoma of the invention, for example, a product containing green chiretta to which an indication that the product prevents or treats glaucoma or clears the visual field, or the like is attached can be used. The act of attaching the indication includes mention on a product body, a container, a packaging, or the like, mention in a document disclosing the product information such as an instruction, a package insert, a pamphlet, or other printed matter, mention in an advertisement used for promotion including various flyers and the Internet, and the like.

In the method for treating glaucoma of the invention, when green chiretta is administered to a mammal, for example, a human, a dose of 1,200 mg or more in terms of green chiretta (21.6 mg or more in terms of andrographolide), preferably 1,200 to 2,400 mg in terms of green chiretta (21.6 to 43.2 mg in terms of andrographolide) is administered twice in the morning and evening, or three times in the morning, afternoon, and evening. It goes without saying that the dose can be changed as appropriate depending on the symptoms. The daily dose is preferably 3,600 mg or more as in terms of green chiretta (64.8 mg or more in terms of andrographolide), more preferably 3,600 to 7,200 mg in terms of green chiretta (64.8 to 129.6 mg in terms of andrographolide). It is preferred to continue ingesting green chiretta for at least 5 days or more, preferably 14 days or more, more preferably 1 month or more.

The above-mentioned green chiretta can treat glaucoma, and at the same time or separately, can also lower intraocular pressure. Therefore, the method for lowering intraocular pressure of the invention can prevent or treat optic nerve damage caused by high intraocular pressure and a disease associated therewith such as ocular hypertension. Further, the method for lowering intraocular pressure of the invention can also prevent an increase in intraocular pressure after glaucoma surgery.

In the method for lowering intraocular pressure of the invention, green chiretta may be administered to a mammal in the same manner as the method for treating glaucoma of the invention described above.

In the method for lowering intraocular pressure of the invention, for example, a product containing green chiretta to which an indication that the product lowers intraocular pressure is attached can be used. The act of attaching the indication includes mention on a product body, a container, a packaging, or the like, mention in a document disclosing the product information such as an instruction, a package insert, a pamphlet, or other printed matter, mention in an advertisement used for promotion including various flyers and the Internet, and the like.

EXAMPLES

Hereinafter, the invention will be described in detail with reference to Examples, but the invention is by no means limited to these Examples.

Production Example 1

Production of Green Chiretta Capsule:

Leaves of green chiretta were cut to an appropriate size, sterilized, and then ground to about 100 to several hundreds of micrometers with a hammer mill, thereby obtaining a fine powder of leaves of green chiretta. The content of andrographolide in the fine powder of leaves of green chiretta was measured by HPLC and was found to be 5.4 mass %. In a No. 1 transparent hard capsule (made of gelatin), 300 mg of the fine powder of leaves of green chiretta was filled and enclosed with hydrogenated rapeseed oil according to a conventional method, thereby producing a green chiretta capsule.

Example 1

Glaucoma Improvement Test:

Patients A to H who have developed glaucoma were made to ingest 5 green chiretta capsules obtained in Production Example 1 in the morning, afternoon, and evening (patients A, B, E, F, G, and H) or in the morning and evening (patients C and D) for 2 months or more. Diagnosis made by an ophthalmologist and test results or subjective evaluation made by the patients themselves before and after ingestion of the capsules were recorded. In a case where only one intraocular pressure is shown, the intraocular pressure is the average value.

(1) Patient A

Before Ingestion:

Patient A started having difficulty seeing the visual field and visited an ophthalmology clinic and was diagnosed with glaucoma. The eye drop did not improve the condition. The intraocular pressure was measured and verbally reported to be 26 mmHg.

After Ingestion:

After about 15 days of ingestion, the eyes became more comfortable and Patient A was able to have clear and sharp vision. It became easier to have a clear visual field and after 4 months, Patient A could have most of the visual field. The intraocular pressure was measured after 4 months and verbally reported to be 17 mmHg.

(2) Patient B

Before Ingestion:

Patient B was diagnosed with glaucoma 10 years ago and had an intraocular pressure of 20 mmHg. The intraocular pressure increased to 25 mmHg 2 years ago, and therefore, Patient B underwent surgery. The intraocular pressure decreased to 15 mmHg after surgery, but 2 months ago, the intraocular pressure in the left eye increased to 17.5 mmHg, and the intraocular pressure in the right eye increased to 17.0 mmHg.

After Ingestion:

The intraocular pressure was measured after 2 months of ingestion and verbally reported to be 16.5 mmHg. Further, Patient B was told that glaucoma did not progress.

(3) Patient C

Before Ingestion:

A few years ago, Patient C started having difficulty seeing the upper part in the right eye and the lower part in the left eye of the visual field, and visited an ophthalmology clinic and was diagnosed with acute glaucoma attack. Patient C was told that if it got any worse, surgery would be required.

After Ingestion:

It became easier to have a clear visual field after about 10 days of ingestion, and after 3 months, Patient C was able to have most of the visual field.

(4) Patient D

Before Ingestion:

One-third of the visual field in the right eye was missing and Patient D could hardly see. When Patient D visited an ophthalmology clinic, Patient D was diagnosed with primary glaucoma. Patient D was told that if it got worse, Patient D would lose sight in the right eye.

After Ingestion:

After 4 months of ingestion, the visual field in the right eye was improved considerably, so that Patient D no longer had to go to the ophthalmology clinic.

(5) Patient E

Before Ingestion:

Patient E had been diagnosed with glaucoma for 20 years.

After Ingestion:

It was verified that glaucoma did not progress in tests (macular retinal thickness measurement) conducted every three months since ingestion was started. Further, Patient E was told that glaucoma was improved in the test conducted after 18 months of ingestion.

(6) Patient F

Before Ingestion:

Patient F developed glaucoma and was prescribed an eye drop in an ophthalmology clinic. Patient F was using this eye drop, but glaucoma was not improved.

After Ingestion:

It was verified that glaucoma did not progress in tests (macular retinal thickness measurement) conducted every three months since ingestion was started. Further, Patient F was told that glaucoma was improved in 2 areas in the left eye and in almost all areas in the right eye in the macular retinal thickness measurement conducted after 18 months of ingestion.

(7) Patient G

Before Ingestion:

It was found that Patient G had a visual field defect in a lower left area in the right eye, and Patient G was diagnosed with glaucoma in an ophthalmology clinic. Patient G was prescribed an eye drop (Tapros) and further prescribed an eye drop (Aifagan) in the ophthalmology clinic. For the past 6 years since Patient G started going to the ophthalmology clinic, Patient G had regular check-ups and tests. The intraocular pressure was 13 to 14 mmHg, and the area of the visual field defect did not expand. After that, Patient G did not go to the ophthalmology clinic for about 3 years. Before ingestion of green chiretta, Patient G was diagnosed with glaucoma in both eyes.

After Ingestion:

When a test (macular retinal thickness measurement) was conducted after 3 months of ingestion, there was no change in the right eye, but glaucoma in one area in the left eye was improved.

(8) Patient H

Before Ingestion:

When Patient H visited an ophthalmology clinic, Patient H was diagnosed with primary glaucoma. When the intraocular pressure was tested using a non-contact tonometer in the ophthalmology clinic, the average intraocular pressure in the right eye was 15.0 (IOP1:15 (3)) mmHg, and the average intraocular pressure in the left eye was 17.0 (IOP1:17) mmHg.

After Ingestion:

After 2 months of ingestion, the average intraocular pressure in the right eye was 14.0 (IOP1:14 (2)) mmHg, and the average intraocular pressure in the left eye was 13.0 (IOP1: 13 (2)) mmHg, and the intraocular pressure decreased in both eyes. In addition, when a test (macular retinal thickness measurement) was conducted after 4 months of ingestion, glaucoma was improved in 2 areas in the right eye, and in one area in the left eye.

In this manner, the patients diagnosed with glaucoma were able to be cured of glaucoma by ingestion of green chiretta. Further, by ingestion of green chiretta, the intraocular pressure could be lowered as well as glaucoma could be treated.

Example 2

Intraocular Pressure Improvement Test:

Patients I and J who had high intraocular pressure were made to ingest 5 green chiretta capsules obtained in Production Example 1 in the morning, afternoon, and evening for 2 to 4 months. Diagnosis made by an ophthalmologist and test results or subjective evaluation made by the patients themselves before and after ingestion of the capsules were recorded.

(9) Patient I

Before Ingestion:

When Patient I visited an ophthalmology clinic, Patient I was diagnosed with ocular hypertension (had not yet developed glaucoma). When the intraocular pressure was tested using a non-contact tonometer in the ophthalmology clinic, the average intraocular pressure in the right eye was 18.0 (IOP1:18) mmHg, and the average intraocular pressure in the left eye was 17.0 (IOP1:17) mmHg.

After Ingestion:

After 4 months of ingestion, the average intraocular pressure in the right eye was 15.0 (IOP1:15 (2)) mmHg, and the average intraocular pressure in the left eye was 15.0 (IOP1:15) mmHg, and the intraocular pressure decreased in both eyes. In addition, Patient I did not develop glaucoma, therefore, glaucoma could be prevented by lowering the intraocular pressure.

(10) Patient J

Before Ingestion:

When Patient J visited an ophthalmology clinic, Patient J was diagnosed with ocular hypertension. When the intraocular pressure was tested using a non-contact tonometer in the ophthalmology clinic, the average intraocular pressure in the right eye was 23.0 (IOP1:23) mmHg, and the average intraocular pressure in the left eye was 17.0 (IOP1:17) mmHg.

After Ingestion:

After 16 days of ingestion, the average intraocular pressure in the right eye was 20.3 (IOP1:19) mmHg, and the average intraocular pressure in the left eye was 19.0 (IOP1:18) mmHg.

By ingestion of green chiretta, the intraocular pressure could be lowered.

The method for treating glaucoma and the method for lowering intraocular pressure of the invention can be used for treating glaucoma and lowering intraocular pressure.

What is claimed is:

1. A method of treating glaucoma in a human in need thereof comprising administering a therapeutically effective amount of green chiretta to the human in need thereof.

2. The method of claim 1, wherein the glaucoma is open-angle glaucoma.

3. The method of claim 2, wherein the open-angle glaucoma is high-tension glaucoma or normal tension glaucoma.

4. The method according to claim 1, wherein the administering is oral administration.

* * * * *